United States Patent
Huang et al.

(10) Patent No.: US 7,934,832 B2
(45) Date of Patent: May 3, 2011

(54) CHARACTERIZATION OF THE RETINAL NERVE FIBER LAYER

(75) Inventors: Yijun Huang, Pleasantville, NY (US); Tetsuyoshi Royama, Montvale, NJ (US); Alexandre Kotchkin, Ridgewood, NJ (US)

(73) Assignee: Topcon Medical Systems, Inc., Oakland, NJ (US)

( * ) Notice: Subject to any disclaimer, the term of this patent is extended or adjusted under 35 U.S.C. 154(b) by 211 days.

(21) Appl. No.: 12/176,550

(22) Filed: Jul. 21, 2008

(65) Prior Publication Data
US 2009/0033868 A1    Feb. 5, 2009

Related U.S. Application Data

(60) Provisional application No. 60/963,054, filed on Aug. 2, 2007.

(51) Int. Cl.
A61B 3/10    (2006.01)
(52) U.S. Cl. .................................................. 351/205
(58) Field of Classification Search .............. 351/205, 351/206, 207, 210, 211, 212, 240–246
See application file for complete search history.

(56) References Cited

U.S. PATENT DOCUMENTS

| | | |
|---|---|---|
| 2005/0018133 A1 | 1/2005 | Huang et al. |
| 2005/0094099 A1 | 5/2005 | Newman et al. |

OTHER PUBLICATIONS

B. Cense, et. al. "Thickness and Birefringence of Healthy Retinal Nerve Fiber Layer Tissue Measured with Polarization-Sensitive Optical Coherence Tomography." Investigative Ophthalmology & Visual Science, Aug. 2004, vol. 45, No. 8, pp. 2606-2612.
M. Gabriele, et al. "Peripapillary Nerve Fiber Layer Thickness Profile Determined with High Speed, Ultrahigh Resolution Optical Coherence Tomography High-Density Scanning." Investigative Ophthalmology & Visual Science, Jul. 2007, vol. 48, No. 7, pp. 3154-3160.
G. Garcia-Sanchez, et. al. "Measurement of retinal nerve fiber layer thickness in normal glaucomatous Cocker Spaniels by scanning laser polarimetry." Veterinary Ophthalmology (2007) 10, Supplement 1, pp. 78-87.
D. Garway-Heath, et al. "Mapping the Visual Field to the Optic Disc in Normal Tension Glaucoma Eyes." Ophthalmology 2000; 107: pp. 1809-1815.
H. Ishikawa, et. al. "Retinal Nerve Fiber Layer Assessment Using Optical Coherence Tomography with Active Optic Nerve Head Tracking." Investigative Opthalmology & Visual Science, Mar. 2006, vol. 47, No. 3, pp. 964-967.

(Continued)

*Primary Examiner* — Ricky L Mack
*Assistant Examiner* — Tuyen Q Tra
(74) *Attorney, Agent, or Firm* — Wolff & Samson PC

(57) ABSTRACT

Disclosed are method and apparatus for characterizing the retinal nerve fiber layer (RNFL). An advantageous diagnostic parameter for characterizing the RNFL is a function of the product of the local RNFL thickness at a measurement locus× the distance of the measurement locus from a base point. The value of the diagnostic parameter in a patient's retina is compared to a corresponding reference range acquired from a population of healthy retinas.

13 Claims, 5 Drawing Sheets

OTHER PUBLICATIONS

Costa, Rogerio A., "Retinal Assessment Using Optical Coherence Tomography", Progress in Retinal and Eye Research, vol. 25, No. 3, May 1, 2006.

Tan, Ou, et al., "Mapping of Macular Substructures with Optical Coherence Tomography for Glaucoma Diagnosis", Ophtalmology, J.B. Lippincott Co., vol. 115, No. 6, Jun. 1, 2008.

PCT International Search Report corresponding to PCT Patent Application PCT/US2008/009153 filed Jul. 29, 2008 (5 pages).

PCT Written Opinion of the International Searching Authority corresponding to PCT Patent Application PCT/US2008/009153 filed Jul. 29, 2008 (8 pages).

U.S. Appl. No. 11/800,186, filed May 4, 2007.

CHARACTERIZATION OF THE RETINAL NERVE FIBER LAYER

This application claims the benefit of U.S. Provisional Application No. 60/963,054 filed Aug. 2, 2007, which is incorporated herein by reference.

BACKGROUND OF THE INVENTION

The present invention relates generally to ophthalmic diagnostics, and more particularly to characterization of the retinal nerve fiber layer.

In the human retina, the optic disc is a specialized ocular structure in which the neural axons of the ganglion cells are gathered as bundles and leave the ocular globe. The retinal nerve fiber layer (RNFL) comprises ganglion cell axon bundles. The thickness of the RNFL increases as it gets closer in proximity to the optic disc.

Analysis of the morphological structure of the RNFL at and around the optic disc provides important clinical information for diagnosing diseases affecting the optic disc. In a healthy optic disc, a reference set of structures in the RNFL is present. One parameter characterizing the structures is the local thickness of the RNFL. In a diseased optic disc, such as that present in glaucoma patients, defects may correspond to changes in the RNFL structures. Some structures may be less pronounced, or, in some instances, absent altogether. Several ocular imaging modalities (for example, optical coherence tomography (OCT), scanning laser ophthalmoscopy, and scanning laser polarimetry) have been used to measure the RNFL thickness in vivo. Clinical studies have reported significant correlation between local variations in RNFL thickness with some ocular defects, for example, visual field loss.

As discussed above, various instruments may be used to measure the RNFL thickness. The RNFL thickness is dependent on the loci (points on the retina) at which the measurements are made. The RNFL thickness varies as a function of position at and around the optic disc. This functional dependence has been studied both by histology evaluation and by OCT. One method for diagnosing eye diseases is to compare the local RNFL thickness (at a set of measurement loci) of a patient's eye with a reference range of local RNFL thicknesses (at a corresponding set of measurement loci) measured from a population of healthy eyes.

Since the local RNFL thickness is a function of the measurement loci relative to the center of the optic disc, or other reference point in the retina, comparisons of the patient's data with the reference range must be determined at the same corresponding measurement loci. Errors will arise if the measurement loci in the patient's eye do not map properly to the corresponding measurement loci used for the reference range. For example, in the Zeiss Stratus OCT 3 instrument, a commonly used instrument in the field of ophthalmology, the RNFL thickness is measured at loci on a circle around the optic disc. The radius of the circle, relative to the center of the optic disc, is fixed at 1.73 mm. Since the precise center of the optic disc may be difficult to establish, and since there is typically eye movement during examination, in practice, the actual distance between the measurement loci and the center of the optic disc may vary from the target value of 1.73 mm. As a result, the reference range representative of the local RNFL thickness at a set of measurement loci in a population of healthy retinas may be broad. The resolution in detecting local variations relative to the reference range is therefore reduced.

What is needed is method and apparatus which has high sensitivity in detecting abnormalities in the RNFL and which has reduced sensitivity (relative to previous diagnostic techniques) to errors in the position of measurement loci. Method and apparatus which may utilize the existing reference range representative of the local RNFL thickness at a set of measurement loci in a population of healthy retinas are further advantageous.

BRIEF SUMMARY OF THE INVENTION

An advantageous diagnostic parameter for characterizing the retinal nerve fiber layer (RNFL) is a function of the product of a local RNFL thickness at a measurement locus×a distance of the measurement locus from a base point. The value of the diagnostic parameter in a patient's retina is compared to a corresponding reference range acquired from a population of healthy retinas. The diagnostic parameter has a high sensitivity in detecting abnormalities in the RNFL. At the same time, the diagnostic parameter is weakly dependent on position in a neighborhood around a measurement locus.

These and other advantages of the invention will be apparent to those of ordinary skill in the art by reference to the following detailed description and the accompanying drawings.

DETAILED DESCRIPTION

Figure 1A:
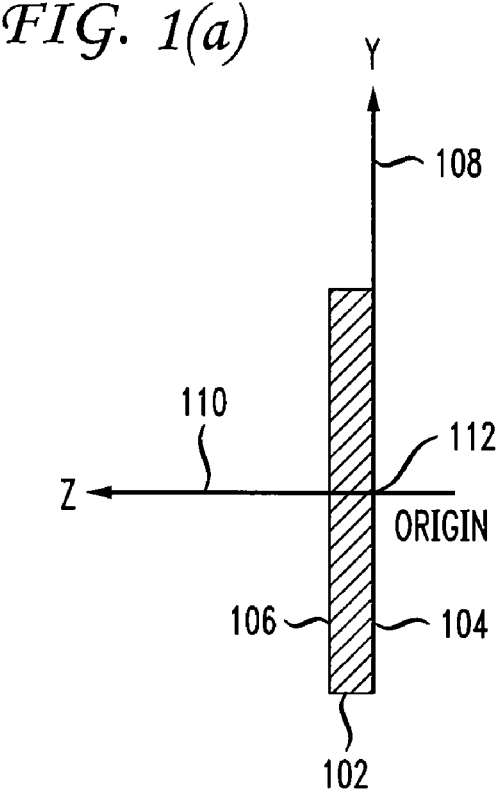
FIG. 1(a) and FIG. 1(b) show schematics of the coordinate system for retinal measurements.

For characterization of the retinal nerve fiber layer (RNFL), a diagnostic parameter which has high sensitivity in detecting abnormalities in the RNFL is advantageous. Herein, a diagnostic parameter is also referred to as a characterization parameter. The difference between the value of the diagnostic parameter at a measurement locus in a patient's retina and a set of reference values may be used to characterize possible defects in the patient's retina. In general, a set of reference values is determined from a previous set of measurements at corresponding measurement loci. Herein, a measurement locus on one retina corresponds to a measurement locus on a second retina if the position of the measurement locus on the first retina, relative to an anatomical feature on the first retina, is the same as the position of the measurement locus on the second retina, relative to the same anatomical feature on the second retina. For example, if the origin of a Cartesian coordinate system (see below) on the first retina is located at the center of the optic disc on the first retina, and if the origin of a Cartesian coordinate system on the second retina is located at the center of the optic disc on the second retina, then a measurement locus on the first retina corresponds to a measurement locus on the second retina if their Cartesian coordinates are the same (assuming the two Cartesian coordinate systems have the same orientation). Herein, the first retina and the second retina may refer to two physically distinct retinas, or to the same physical retina at different times.

If the diagnostic parameter is measured over a set of corresponding measurement loci, in general, there may be a statistical distribution of the values of the diagnostic parameter. From this statistical distribution, a reference range for the diagnostic parameter may be determined. Herein, this reference range "corresponds" to a measurement locus, and the reference range is also referred to as the corresponding reference range at a measurement locus. Of particular interest is a reference range determined from a set of measurements acquired from a population of healthy retinas. Herein, this range of values is referred to as the healthy reference range. If the measured value of the diagnostic parameter falls outside of the healthy reference range, further examination of the retina may be warranted. A reference range may also be determined from a set of measurements acquired from a population of retinas inflicted with specific disorders.

In an embodiment, a reference range is calculated from previous measurement values stored in a database. The previous measurement values may have been acquired from a single source (such as measurements performed by one ophthalmologist) or from a combination of sources (such as measurements from multiple group studies). In an embodiment, the database may be stored in a data storage unit (such as a hard drive) in a computer, and the reference range may be calculated by the computer executing a user-specified computer program. Further details of a computer system for performing diagnostics are discussed below.

Comparison of a measured value with a reference range may be performed either by a user or by a diagnostic system. In an embodiment, if an ophthalmologist determines that the measured value falls outside of the healthy reference range, he may order additional diagnostic tests or more frequent examinations. In an embodiment, if the measured value falls outside of the healthy reference range, a diagnostic system may issue an alert to a user. For example, if the measured value and the healthy reference range are printed on a printer, a measured value falling outside of the healthy reference range may be printed in red ink. As another example, if the measured value and the healthy reference range are displayed on a monitor, a flashing red alert message may be displayed if a measured value falls outside of the healthy reference range. In response to an alert, an ophthalmologist may order additional diagnostic tests. In an embodiment, a diagnostic system (for example, a computer-controlled diagnostic system), in response to an alert, may specify additional diagnostic tests, which, may, for example, depend on the measured value relative to the healthy reference range.

At the same time, a diagnostic parameter which is invariant (or weakly dependent) on the position within a neighborhood around a desired measurement locus is advantageous to reduce errors introduced by eye movement or instrument misalignment, for example. The size and shape of the neighborhood is dependent on the required accuracy specified by a user, such as an ophthalmologist. As discussed above, a routine diagnostic parameter is RNFL thickness, but this is susceptible to minor variations in the measurement locus.

Figure 1B:
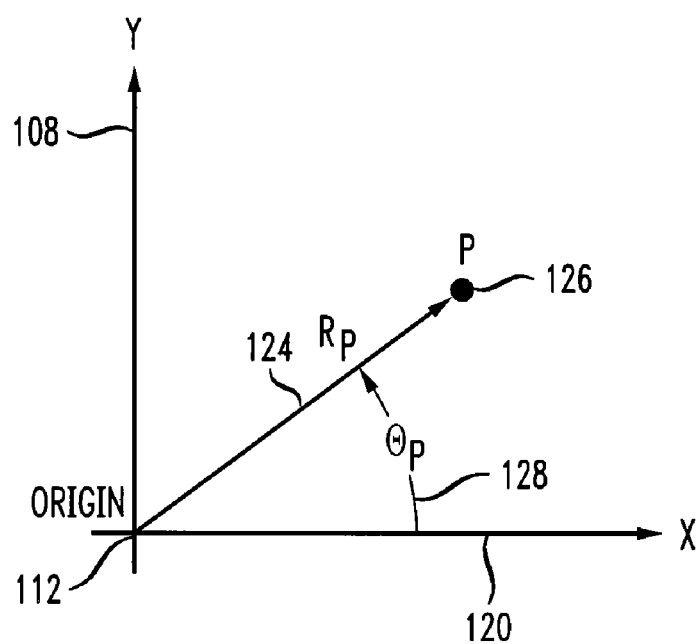

FIG. 1(a) and FIG. 1(b) show the reference geometry used in the discussions below. FIG. 1(a) is a cross-sectional view, and FIG. 1(b) is a frontal view. Although a retina is a curved structure, it may be approximated by a planar structure, as represented in FIG. 1(a) by cross-section plane 102 with front surface plane 104 and rear surface plane 106. The front surface plane 104, for example, may be that which is viewed by an observer through an ophthalmoscope or photographed by a fundus camera. In a standard Cartesian coordinate system, the cross-section plane 102, as shown in FIG. 1(a), is the Y-Z plane, indicated by Y-axis 108 and Z-axis 110. The positive direction of Z runs from the front surface plane 104 to the rear surface plane 106, with Z=0 defined at the front surface plane 104. The Z-coordinate indicates the depth of a layer below the front surface plane 104.

The front surface plane 104 in FIG. 1(a), viewed along the +Z direction, is represented in FIG. 1(b) by the X-Y plane, indicated by X-axis 120 and Y-axis 108. Herein, the X-Y plane is also referred to as the retinal plane. In FIG. 1(a) and FIG. 1(b), the origin is denoted by Origin 112. The position of Origin 112 in the X-Y plane may be specified by a user, such as an ophthalmologist. For example, Origin 112 may be placed at the center of the optic disc. In FIG. 1(b), the position of a locus, such as point P 126, on the X-Y plane is specified by the polar coordinates $(R_P, \theta_P)$, with radius $R_P$ 124 and polar angle $\theta_P$ 128.

The inventors have determined that, as the retinal nerve fiber bundles approach the optic nerve head, the cross-sectional areas of interest (details of which are discussed below) through which the RNFL bundles pass remain constant, or nearly constant, while the thickness varies in value. A cross-sectional area of interest is referenced with respect to a plane of interest which intersects the X-Y plane such that the intersection line passes through the locus of interest. Herein, the locus of interest is also referred to as the measurement locus; the plane of interest is also referred to as the measurement plane; and the cross-sectional area of interest is also referred to as the measurement cross-sectional area. For example, the measurement plane may be orthogonal to the X-Y plane (parallel to the Z-axis), such as cross-section plane 102 in FIG. 1(a). In general, the measurement plane is oblique to the X-Y plane (inclined with respect to the Z-axis). As discussed below, the relationship between the measurement cross-sectional area and the RNFL thickness at a set of measurement loci may be modeled mathematically. An advantageous diagnostic parameter may be calculated from the geometry of the RNFL structures.

In an embodiment, an advantageous diagnostic parameter A is a function of the product of the local RNFL thickness at a measurement locus×the distance of the measurement locus from a base point in the retina (as discussed below, a set of base points may be specified). Herein, the term base point is a generalization of the term reference point.

$$A(R_M, \theta_M) = A[L(R_M, \theta_M) \times T(R_M, \theta_M)], \qquad \text{Eqn. 1}$$

where $(R_M, \theta_M)$ are the polar coordinates of a measurement locus M in the X-Y plane;

$L(R_M, \theta_M)$ is the distance of the measurement locus from a base point; and $T(R_M, \theta_M)$ is the local thickness of the RNFL at the measurement locus.

Note that, in general, the parameter $A(R_M, \theta_M)$ is explicitly a function of $\theta_M$, since RNFL structures may be axially asymmetric about the Z-axis. As discussed below, Eqn. 1 may be derived from a mathematical model of the RNFL structure. It may also be derived from empirical measurements, or determined heuristically. The dependence of the diagnostic parameter A on structures in the RNFL is sufficiently strong to detect differences between the RNFL in a healthy eye and the RNFL in a diseased eye. At the same time, the diagnostic parameter A is invariant, or weakly dependent, on the position within a neighborhood around a desired measurement locus. The size and shape of the neighborhood is dependent on the required accuracy specified by a user, such as an ophthalmologist.

In an embodiment, the diagnostic parameter $A(R_M, \theta_M)$ may be determined from the mathematical relationship $$A(R_M,\theta_M)=c(R_M,\theta_M)\times L(R_M,\theta_M)\times T(R_M,\theta_M) \qquad \text{Eqn. 2}$$

The parameter $c(R_M, \theta_M)$ is a general coefficient function. In some instances, $c(R_M, \theta_M)$ is a constant, which may be normalized to 1. In general, there is a set of base points from which $L(R_M, \theta_M)$ may be measured. In some instances, $L(R_M, \theta_M)$ is measured from a single base point. Examples are discussed below.

Figure 2A:
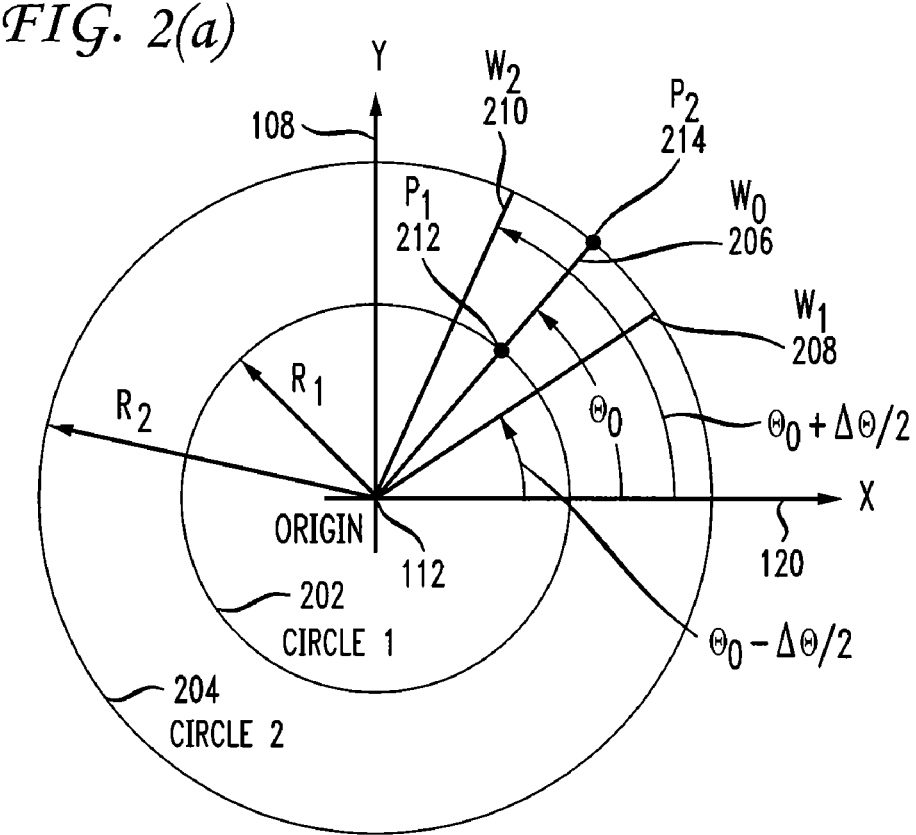
FIG. 2(a)-FIG. 2(c) show schematics for retinal nerve fiber layer characterization with a single base point at the origin.
Figure 2B:
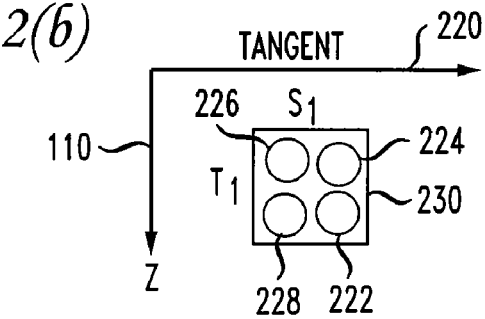
Figure 2C:
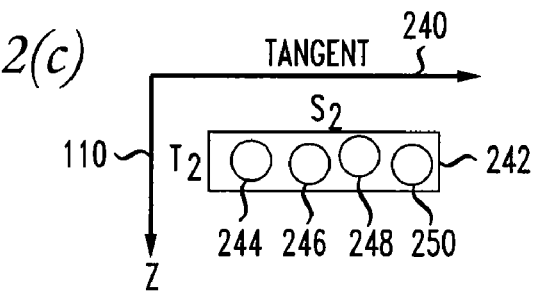

FIG. 2(a)-FIG. 2(c) illustrate an example in which the optic disc (not shown) is uniformly circular. Shown are two concentric circles. The inner circle, Circle 1 202, with radius $R_1$, for example, may represent a first set of measurement loci around the optic disc, centered at the Origin 112. The outer circle, Circle 2 204, with radius $R_2$, for example, may represent a second set of measurement loci. The first measurement locus $P_1$ 212 [with polar coordinates $(R_1, \theta_0)$] represents a measurement locus on Circle 1 202. Similarly, the second locus $P_2$ 214 [with polar coordinates $(R_1, \theta_0)$] represents a measurement locus on Circle 2 204. Shown in FIG. 2(a) are three radial lines, $W_0$ 206, $W_1$ 208, and $W_2$ 210, with polar angles $\theta_0$, $\theta_0-\Delta\theta/2$, and $\theta_0+\Delta\theta/2$, respectively. The first measurement locus $P_1$ 212 and the second measurement locus $P_2$ 214 both lie on the radial line $W_0$ 206.

The radial lines $W_1$ 208 and $W_2$ 210 bound a sector. Within the sector, the arc on Circle 1 202 bounded by $W_1$ 208 and $W_2$ 210, denoted Arc 1 (not shown), has an arc length $S_1=R_1\Delta\theta$, since the angle subtended between $W_1$ 208 and $W_2$ 210 is $\Delta\theta$. Similarly, the arc on Circle 2 bounded by $W_1$ 208 and $W_2$ 210, denoted Arc 2 (not shown), has an arc length $S_2=R_2\Delta\theta$. In this example, the +Z-Axis points down into the X-Y plane of the figure, and the measurement planes (not shown) at measurement locus $P_1$ 212 and at measurement locus $P_2$ 214 are orthogonal to the X-Y plane. The thickness of the RNFL, denoted as T, is measured along the +Z-Axis. As $\Delta\theta \to 0$, the measurement plane at measurement locus $P_1$ 212 intersects the X-Y plane along the tangent to Arc 1 at measurement locus $P_1$ 212. Similarly, as $\Delta\theta \to 0$, the measurement plane at locus $P_2$ 214 intersects the X-Y plane along the tangent to Arc 2 at measurement locus $P_2$ 214.

The inventors have determined that the measurement cross-sectional area through which the nerve bundles cross is constant, or nearly constant. This may hold true over at least the peripapillary area, approximately 2.5 mm to 4.5 mm in diameter, centered on the optic disc. In the example shown in FIG. 2(a)-FIG. 2(c), the nerve bundles fan out from Circle 1 202 to Circle 2 204. FIG. 2(b) is a schematic of the measurement cross-sectional area 230 at measurement locus $P_1$ 212 bounded by Arc 1 and by the local upper and lower boundaries (along the Z-axis) of the RNFL. If $\Delta\theta$ is sufficiently small, the measurement cross-sectional area 230 is approximated by a rectangular region with length $S_1$ along the tangent to Arc 1 at the measurement locus $P_1$ 212, denoted herein as Tangent 220, and height (thickness) $T=T_1$, where $T_1$ is the local thickness of the RNFL at measurement locus $P_1$ 212. Similarly, FIG. 2(c) is a schematic of the measurement cross-sectional area bounded by Arc 2 and by the local upper and lower boundaries (along the Z-axis) of the RNFL. If $\Delta\theta$ is sufficiently small, the measurement cross-sectional area 242 is approximated by a rectangular region with length $S_2$ along the tangent to Arc 2 at the measurement locus $P_2$ 214, denoted herein as Tangent 240, and height (thickness) $T=T_2$, where $T_2$ is the local thickness of the RNFL at measurement locus $P_2$ 214.

The inventors have determined that the two measurement cross-sectional areas are equal. Therefore, a relationship between R and T at $P_1$ 212 and $P_2$ 214 may be derived:

$$A_1=S_1T_1=R_1(\Delta\theta)T_1 \qquad \text{Eqn. 3}$$

$$A_2=S_2T_2=R_2(\Delta\theta)T_2 \qquad \text{Eqn. 4}$$

$$A_1=A_2 \qquad \text{Eqn. 5}$$

$$R_1(\Delta\theta)T_1=R_2(\Delta\theta)T_2 \qquad \text{Eqn. 6}$$

$$R_1T_1=R_2T_2 \qquad \text{Eqn. 7}$$

$$T_2=(R_1/R_2)T_1 \qquad \text{Eqn. 8}$$

Eqn. 3-Eqn. 5 have a direct physical interpretation. In FIG. 2(b), nerve fiber bundles 222-228 at measurement locus $P_1$ 212 pass through the measurement cross-sectional area 230 at locus $P_1$ 212. In FIG. 2(c), the nerve fiber bundles 244-250 pass through the measurement cross-sectional area 242 at locus $P_2$ 214. Nerve fiber bundles 244-250 correspond to nerve fiber bundles 222-228, except that their geometry has been reconfigured. Since the arc length S decreases as the bundles approach the center of the optic disc, the local thickness T of the RNFL increases to maintain a constant, or near constant, value for the number of nerve fiber bundles/(unit cross-sectional area).

In an embodiment, the relationship in Eqn. 8 may be used to derive a reference range of RNFL thicknesses corresponding to measurement loci which differ from the reference range of RNFL thicknesses acquired at standard measurement loci. For example, as discussed above, the Zeiss Stratus OCT 3 instrument is a commonly used instrument in the field of ophthalmology, and it has been used to acquire a set of measurements from which a historical reference range of the RNFL thickness from a large population of healthy retinas has been derived. Herein, this historical reference range is referred to as the historical healthy reference range. This historical healthy reference range, however, is limited to a set of measurement loci falling on a circle whose center is at the center of the optic disc and whose radius is fixed at 1.73 mm. Note that, in general, the RNFL thickness is axially asymmetric about the Z-axis. The historical healthy reference range has been acquired at multiple polar angles. One skilled in the art may determine other historical reference ranges.

With advances in spectral domain three-dimensional optical coherence tomography (3D-OCT), however, a 3-D volume dataset characterizing the retinal structure may be readily measured. From the 3-D volume dataset, the RNFL thickness over a range of radii (at a particular polar angle) may be determined. Using the relationship in Eqn. 8, a reference range of RNFL thicknesses corresponding to measurement loci over a range of radii may be derived from a historical reference range acquired at a single fixed radius (at a particular polar angle). In an embodiment, $(R_M, \theta_M)$ are the polar coordinates of a measurement locus; $<T_M(R_M, \theta_M)>$ is a reference range of RNFL thicknesses at the measurement locus $(R_M, \theta_M)$; $(R_H, \theta_H=\theta_M)$ are the polar coordinates at which a corresponding historical reference range of RNFL thicknesses has been acquired; and $<T_H(R_H, \theta_M)>$ is a historical reference range of thicknesses acquired at $(R_H, \theta_M)$. From Eqn. 8, the following relationship may be derived:

$$<T_M(R_M,\theta_M)>=<T_H(R_H,\theta_M)>R_H/R_M \qquad \text{Eqn. 8(a)}$$

A reference range over a range of radii may be derived from a historical reference range via several modes. For example, it may be calculated dynamically when data from a patient is processed. It may also be calculated statically and used to populate a look-up table, which, for example, may be stored in a database. For a specific patient, the RNFL thickness at a set of measurement loci over a range of radii may then be compared to the reference range derived from the historical reference range. Characterizing the RNFL thickness over a range of radii may provide a more thorough diagnosis than characterizing the RNFL thickness at a single fixed radius. In particular, for a specific patient, the RNFL thickness at a set of measurement loci over a range of radii may be compared to the healthy reference range derived from the historical healthy reference range.

Figure 3:
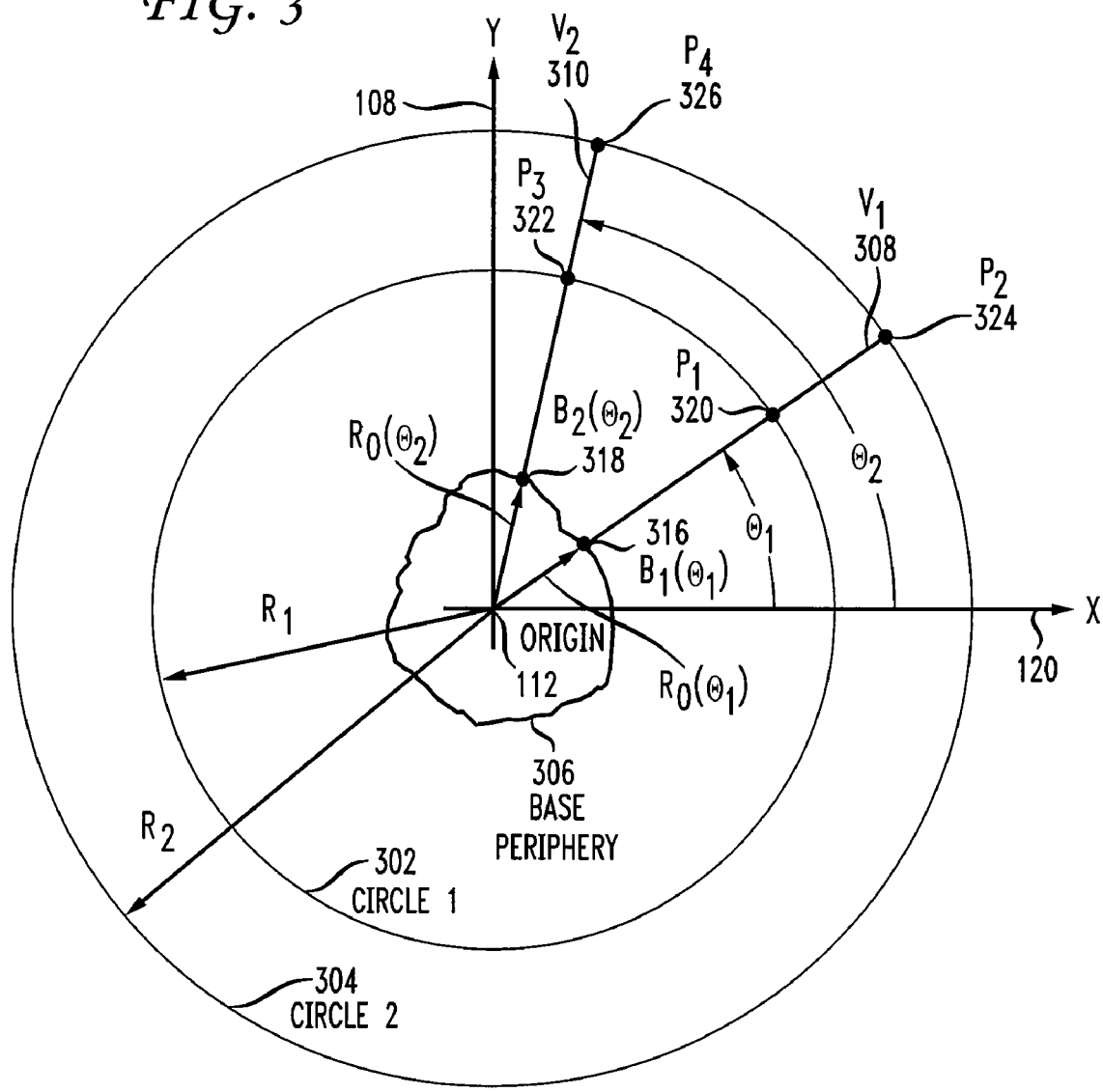
FIG. 3 shows a schematic for retinal nerve fiber layer characterization with a set of base points located on a base periphery.

FIG. 3 illustrates an example with an irregular geometry. The Base Periphery 306 is defined by the function $R=R_0(\theta)$. The Base Periphery 306, for example, may represent the periphery of an irregular optic disc. In this example, the two circles, Circle 1 302 and Circle 2 304, represent two sets of measurement loci. The distance of a measurement locus is the radial distance between the measurement locus and a base point on the Base Periphery 306. That is, the distance of a measurement locus is not measured from the Origin 112. For example, along the radial line $V_1$ 308, with polar angle $\theta_1$, the base point is $B_1(\theta_1)$ 316 ($R=R_0(\theta_1)$, $\theta=\theta_1$). The distance between measurement locus $P_1$ 320 ($R=R_1$, $\theta=\theta_1$) and base point $B_1(\theta_1)$ 316 is $[R_1-R_0(\theta_1)]$. The distance between measurement locus $P_2$ 324 ($R=R_2$, $\theta=\theta_1$) and base point $B_1(\theta_1)$ 316 is $[R_2-R_0(\theta_1)]$. Similarly, along the radial line $V_2$ 310, with polar angle $\theta_2$, the base point is $B_2(\theta_2)$ 318 ($R=R_0(\theta_2)$, $\theta=\theta_2$). The distance between measurement locus $P_3$ 322 ($R=R_1$, $\theta=\theta_2$) and base point $B_2(\theta_2)$ 318 is $[R_1-R_0(\theta_2)]$. The distance between measurement locus $P_4$ 326 ($R=R_2$, $\theta=\theta_2$) and base point $B_2(\theta_2)$ 318 is $[R_2-R_0(\theta_2)]$. An analysis similar to that previously discussed in reference to FIG. 2(a)-FIG. 2(c) yields:

at $\theta=\theta_1$, $$A(\theta_1)=[R_1-R_0(\theta_0)]T_1=[R_2-R_0(\theta_1)]T_2 \quad \text{Eqn. 9}$$

$$T_2/T_1=[R_1-R_0(\theta_1)]/[R_2-R_0(\theta_1)] \quad \text{Eqn. 10}$$

at $\theta=\theta_2$, $$A(\theta_2)=[R_1-R_0(\theta_2)]T_3=[R_2-R_0(\theta_2)]T_4 \quad \text{Eqn. 11}$$

$$T_4/T_3=[R_1-R_0(\theta_2)]/[R_2-R_0(\theta_2)] \quad \text{Eqn. 12}$$

where $T_1$-$T_4$ are the local RNFL thicknesses at measurement loci $P_1$ 320, $P_2$ 324, $P_3$ 322, and $P_4$ 326, respectively.

Figure 4:
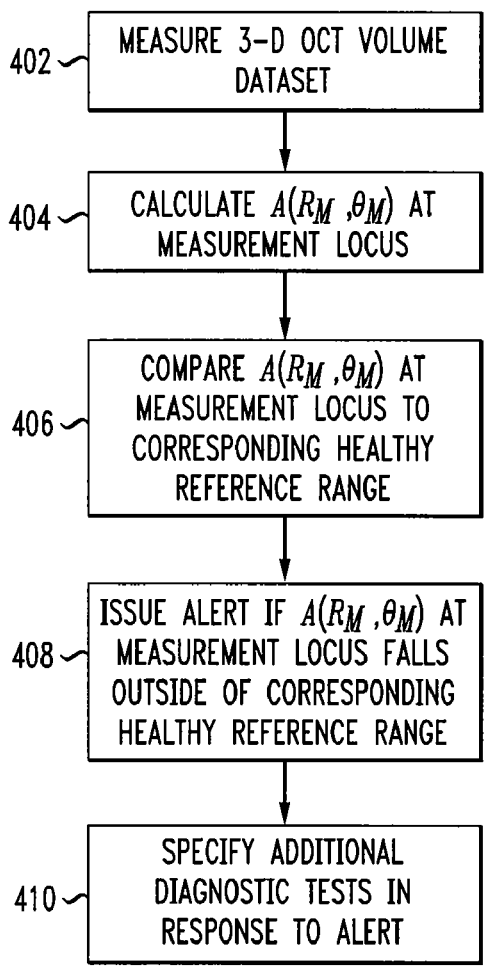
FIG. 4 shows a flowchart of steps for characterizing a retinal nerve fiber layer using the diagnostic parameter A.

FIG. 4 shows a flowchart of steps of an embodiment for characterizing a RNFL structure using the parameter $A(R, \theta)$. In step 402, a patient's retina is measured by 3-D OCT, and a 3-D volume dataset is measured. One skilled in the art may also characterize the retina by other modalities. The process then passes to step 404, in which the value of the parameter $A(R_M, \theta_M)$ is calculated from the 3-D volume dataset at a measurement locus $(R_M, \theta_M)$. As discussed above, the parameter $A(R, \theta)$ may be expressed mathematically in different functional forms, depending on the retinal geometry. The process then passes to step 406, in which the value of the parameter $A(R_M, \theta_M)$ at the measurement locus $(R_M, \theta_M)$ on the patient's retina is compared to a healthy reference range of $A(R_M, \theta_M)$ determined from previous measurements from a population of healthy retinas. The process then passes to step 408. If the value of the parameter falls outside of the healthy reference range, an alert is issued. In step 410, in response to the alert, additional diagnostic tests are specified.

Figure 5:
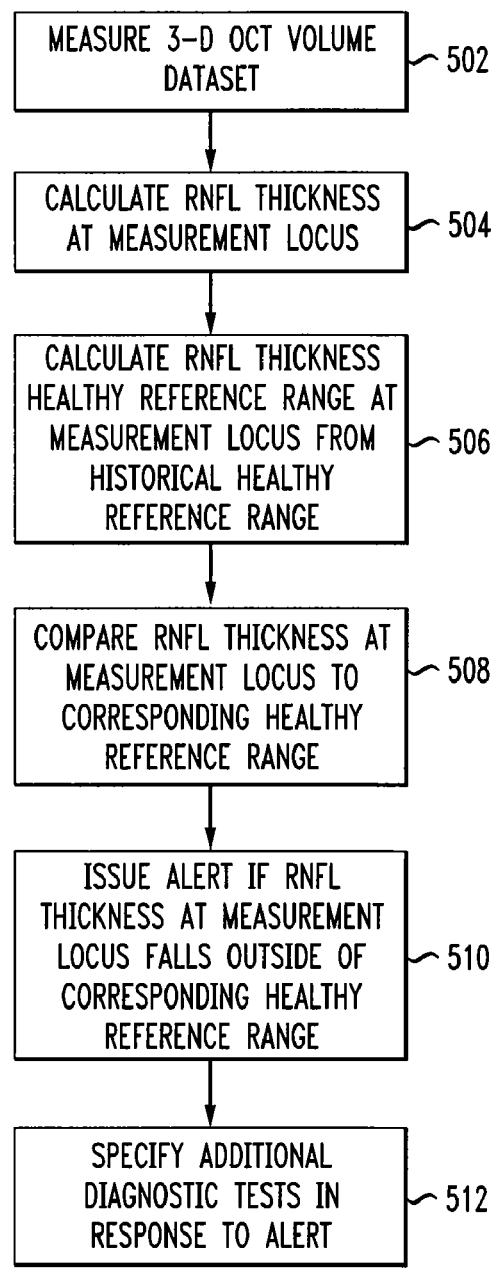
FIG. 5 shows a flowchart of steps for comparing the retinal nerve fiber thickness at a measurement locus with a reference range.

FIG. 5 shows a flowchart of steps of an embodiment for characterizing the RNFL thickness of a patient's retina. In step 502, a patient's retina is measured by 3-D OCT, and a 3-D volume dataset is measured. One skilled in the art may also characterize the retina by other modalities. The process then passes to step 504, in which the value of the RNFL thickness is calculated from the 3-D volume dataset at a measurement locus $(R_M, \theta_M)$. The process then passes to step 506, in which the RNFL thickness healthy reference range at the corresponding measurement locus in a population of healthy retinas is calculated from the RNFL thickness historical healthy reference range measured by other modalities, such as by the Zeiss Stratus OCT 3, and the mathematical relationship in Eqn. 8(a). The RNFL thickness healthy reference range may also be calculated in advance from the RNFL thickness historical healthy reference range and used to populate a look-up table. The process then passes to step 508, in which the RNFL thickness at the measurement locus $(R_M, \theta_M)$ on the patient's retina is compared to the corresponding RNFL thickness healthy reference range. The process then passes to step 510. If the value of the measured RNFL thickness falls outside of the healthy reference range, an alert is issued. In step 512, in response to the alert, additional diagnostic tests are specified.

Figure 6:
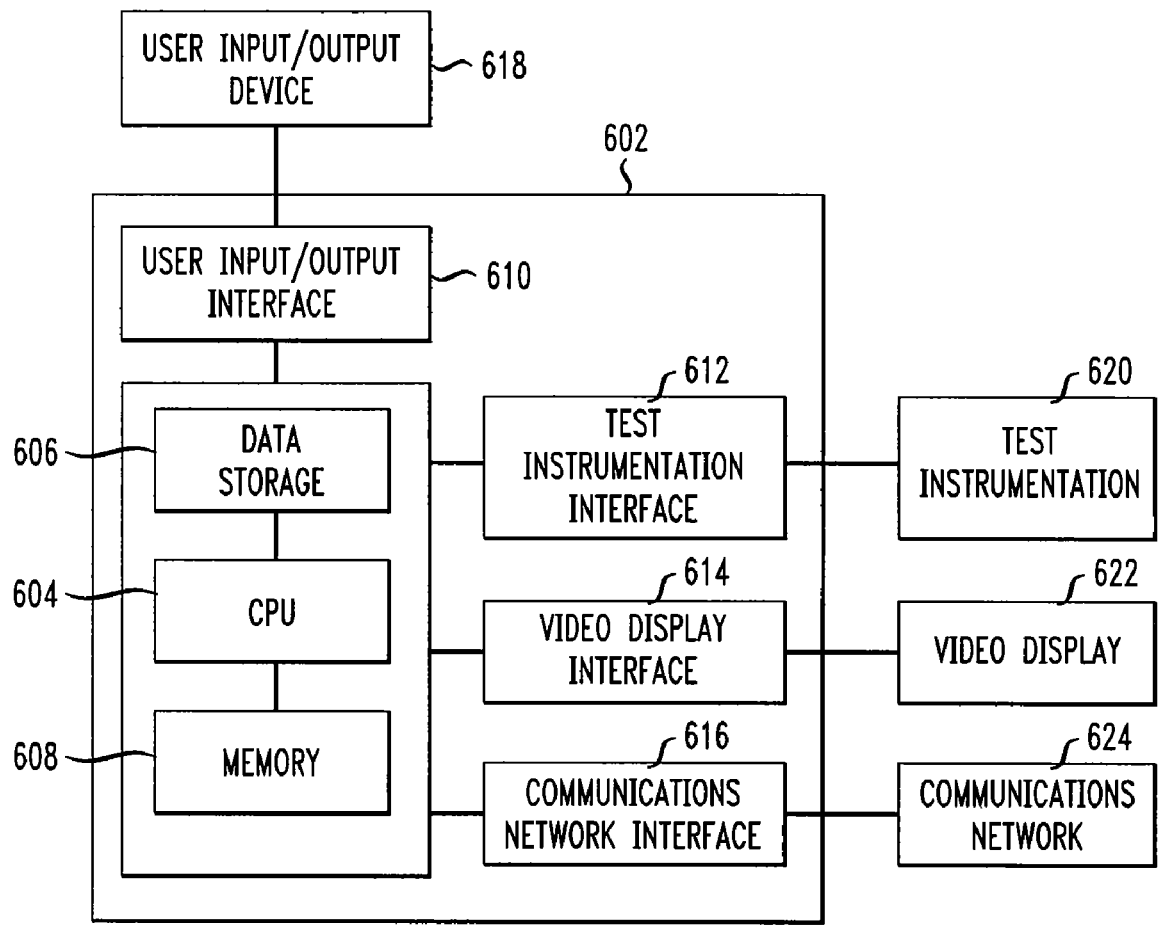
FIG. 6 shows a schematic of a computer-based test measurement system.

One embodiment of a measurement system for characterizing the RNFL may be implemented using a computer. For example, the steps shown in the flowcharts in FIG. 4 and FIG. 5 may be performed using a computer. As shown in FIG. 6, computer 602 may be any type of well-known computer comprising a central processing unit (CPU) 604, memory 608, data storage 606, and user input/output interface 610. Data storage 606 may comprise a hard drive or non-volatile memory. User input/output interface 610 may comprise a connection to a user input device 618, such as a keyboard or mouse. As is well known, a computer operates under control of computer software which defines the overall operation of the computer and applications. CPU 604 controls the overall operation of the computer and applications by executing computer program instructions which define the overall operation and applications. The computer program instructions may be stored in data storage 606 and loaded into memory 608 when execution of the program instructions is desired. Databases such as a set of previous measurements of diagnostic parameters, a historical reference range of RNFL thicknesses, and a look-up table populated with reference ranges of RNFL thicknesses at different measurement loci may also be stored in data storage 606. Computer 602 may further comprise a video display interface 614, which may transform signals from CPU 604 to signals which may drive video display 622. Computer 602 may further comprise one or more network interfaces. For example, communications network interface 624 may comprise a connection to an Internet Protocol (IP) communications network 624, which may transport user or test data.

In an embodiment, computer 602 may further comprise one or more test instrumentation interfaces. For example test instrumentation interface 612 may allow computer 602 to communicate with test instrumentation 620, which may, for example, be a 3-D OCT ophthalmic measurement instrument. In an embodiment, data measured by a 3-D OCT ophthalmic measurement instrument which is not directly interfaced to computer 602 may be transferred to computer 602 via user input/output interface 610 or via communications network interface 616, for example. Computers are well known in the art and will not be described in detail herein.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for characterizing a retinal nerve fiber layer (RNFL), the method comprising the steps of:

calculating a value of a diagnostic parameter according to:

$$A(R_M,\theta_M)=c(R_M,\theta_M)\times L(R_M,\theta_M)\times T(R_M,\theta_M);$$

wherein:
- $(R_M, \theta_M)$ are the polar coordinates of a measurement locus on a retina;
- $A(R_M, \theta_M)$ is the value of said diagnostic parameter at said measurement locus;
- $c(R_M, \theta_M)$ is a coefficient at said measurement locus;
- $L(R_M, \theta_M)$ is the distance between said measurement locus and a base point; and
- $T(R_M, \theta_M)$ is the RNFL thickness at said measurement locus; and comparing the calculated value of the diagnostic parameter to a reference range of the diagnostic parameter.

2. The method of claim 1, further comprising the step of:
determining a healthy reference range of said diagnostic parameter from a population of healthy retinas.

3. The method of claim 2, further comprising the step of:
issuing an alert if said calculated value falls outside of said healthy reference range.

4. The method of claim 3, further comprising the step of:
specifying additional diagnostic tests in response to said alert.

5. The method of claim 1, wherein:
said coefficient is $c(R_M, \theta_M)=1$;
the polar coordinates of said base point are $(R_0(\theta_M), \theta_M)$;
said distance is $L(R_M, \theta_M)=[R_M-R_0(\theta_M)]$; and
the value of said diagnostic parameter is $$A(R_M,\theta_M)=[R_M-R_0(\theta_M)]T(R_M,\theta_M).$$

6. The method of claim 5, wherein:
the polar coordinates of said base point are $(R_0(\theta_M), \theta_M)=(0, 0)$; and
the value of said diagnostic parameter is $$A(R_M,\theta_M)=R_M T(R_M,\theta_M).$$

7. The method of claim 1, further comprising the step of:
determining said measurement locus and said diagnostic parameter from three-dimensional optical coherence tomography.

8. The method of claim 1, further comprising the step of:
determining said reference range from three-dimensional optical coherence tomography.

9. An apparatus for characterizing a retinal nerve fiber layer (RNFL), the apparatus comprising:

means for calculating a value of a diagnostic parameter according to:

$$A(R_M,\theta_M)=c(R_M,\theta_M)\times L(R_M,\theta_M)\times T(R_M,\theta_M);$$

wherein:
- $(R_M, \theta_M)$ are the polar coordinates of a measurement locus on a retina;
- $A(R_M, \theta_M)$ is the value of said diagnostic parameter at said measurement locus;
- $c(R_M, \theta_M)$ is a coefficient at said measurement locus;
- $L(R_M, \theta_M)$ is the distance between said measurement locus and a base point; and
- $T(R_M, \theta_M)$ is the RNFL thickness at said measurement locus; and means for comparing the calculated value of the diagnostic parameter to a reference range of the diagnostic parameter.

10. The apparatus of claim 9, further comprising:
means for determining a healthy reference range of said diagnostic parameter from a population of healthy retinas.

11. The apparatus of claim 10, further comprising:
means for issuing an alert if said calculated value falls outside of said healthy reference range.

12. The apparatus of claim 11, further comprising:
means for specifying additional diagnostic tests in response to said alert.

13. The apparatus of claim 9, further comprising:
means for determining said measurement locus and said RNFL thickness from three-dimensional optical coherence tomography.

* * * * *

UNITED STATES PATENT AND TRADEMARK OFFICE
CERTIFICATE OF CORRECTION

PATENT NO. : 7,934,832 B2
APPLICATION NO. : 12/176550
DATED : May 3, 2011
INVENTOR(S) : Huang et al.

Page 1 of 1

It is certified that error appears in the above-identified patent and that said Letters Patent is hereby corrected as shown below:

Column 7, line 36, "$A(\theta_1)=[R_1-R_0(\theta_0)]T_1=[R_2-R_0(\theta_1)]T_2$" should read
-- $A(\theta_1)=[R_1-R_0(\theta_1)]T_1=[R_2-R_0(\theta_1)]T_2$ --

Signed and Sealed this
Sixteenth Day of August, 2011

David J. Kappos
*Director of the United States Patent and Trademark Office*